(12) United States Patent
Naganuma

(10) Patent No.: US 6,676,686 B2
(45) Date of Patent: Jan. 13, 2004

(54) NONINVASIVE DETECTION AND ACTIVATION OF THE LYMPHATIC SYSTEM IN TREATING DISEASE AND ALLEVIATING PAIN

(76) Inventor: Harumi Naganuma, 15 Fernwood Dr., San Francisco, CA (US) 94127

( * ) Notice: Subject to any disclaimer, the term of this patent is extended or adjusted under 35 U.S.C. 154(b) by 123 days.

(21) Appl. No.: 09/843,463

(22) Filed: Apr. 25, 2001

(65) Prior Publication Data

US 2002/0002387 A1 Jan. 3, 2002

Related U.S. Application Data

(60) Provisional application No. 60/199,531, filed on Apr. 25, 2000.

(51) Int. Cl.⁷ .............................. A61H 7/00; A61N 1/00
(52) U.S. Cl. ........................................... 607/1; 128/898
(58) Field of Search ............................ 607/1, 2, 50, 72, 607/148, 152, 153; 601/152, 133–134; 128/898

(56) References Cited

U.S. PATENT DOCUMENTS

| | | | |
|---|---|---|---|
| 4,827,945 A | | 5/1989 | Groman et al. ............. 424/9.32 |
| 4,957,484 A | | 9/1990 | Murtfeldt ..................... 604/540 |
| 4,976,263 A | | 12/1990 | Seidl et al. .................... 607/63 |
| 4,996,194 A | | 2/1991 | Cohen et al. ............. 424/184.1 |
| 5,109,846 A | * | 5/1992 | Thomas ....................... 607/115 |
| 5,391,143 A | | 2/1995 | Kensey ........................ 327/181 |
| 5,595,743 A | | 1/1997 | Wu .............................. 424/728 |
| 5,672,148 A | | 9/1997 | Maunier ...................... 601/148 |
| 5,732,704 A | | 3/1998 | Thurston et al. ............. 600/431 |
| 5,753,237 A | | 5/1998 | Daynes et al. ............ 424/278.1 |
| 5,817,138 A | | 10/1998 | Suzuki ......................... 607/67 |
| 5,894,844 A | * | 4/1999 | Rohrberg ..................... 128/898 |
| 5,940,888 A | | 8/1999 | Sher .............................. 2/267 |
| 5,961,458 A | | 10/1999 | Carroll ........................ 600/436 |
| 6,179,796 B1 | * | 1/2001 | Waldridge ................... 601/149 |
| 6,366,808 B1 | * | 4/2002 | Schroeppel et al. ........... 607/2 |

OTHER PUBLICATIONS

Tappan, Frances M., "Healing Massage Techniques: A Study of Eastern and Western Methods", Reston Publishing Company, Inc., ©. 1978, p. 19.*

* cited by examiner

*Primary Examiner*—Carl Layno
(74) *Attorney, Agent, or Firm*—Reed & Eberle LLP; Louis L. Wu

(57) ABSTRACT

A method is provided for treating disease and alleviating pain associated with the lymphatic system in a living mammalian body. The method generally relates to a noninvasive method for alleviating a disorder associated with a portion of the lymphatic system, e.g., a lymph node in a living mammalian body, wherein the treatment involves lymphatic activation characterized by localized pulsations at the closest exterior body surface to the activated portion of the lymphatic system. The activation involves placing a stimulation source in physical contact with the closest exterior body surface. In addition, an opposing body surface with respect to the closest exterior body surface is contacted simultaneously with the stimulation source. The stimulation source transfers energy to the affected portion until the localized pulsations substantially subside and/or lymph obstruction is substantially eliminated. This noninvasive method is particularly suited for pain relief and healing.

40 Claims, 2 Drawing Sheets

NONINVASIVE DETECTION AND ACTIVATION OF THE LYMPHATIC SYSTEM IN TREATING DISEASE AND ALLEVIATING PAIN

CROSS-REFERENCE TO RELATED APPLICATIONS

This application claims priority to U.S. Provisional Application No. 60/199,531, filed Apr. 25, 2000.

TECHNICAL FIELD

The present invention relates to a method for treating disease and alleviating pain associated with the lymphatic system in a living mammalian body. More particularly, the present invention relates to a noninvasive method for detecting and activating the lymphatic system wherein the method involves the generation of a pulsation detectable at the closest exterior body surface to an activated lymphatic area.

BACKGROUND

The lymphatic system is a subsidiary of the circulatory system that offers a route for the return of tissue fluid to the bloodstream. The system includes lymph capillaries that begin in tissue to collect tissue fluid, i.e., lymph. The capillaries eventually lead into lymphatic vessels which empty lymph into large veins above the heart. Along the pathway of the lymphatic vessels are specialized structures called lymph nodes. The lymph nodes serve two important purposes—as a filter to prevent the spread of infection and as a source of lymphocytes. In contrast to the cardiovascular system which forms a complete circuit, the lymphatic system is a one-way system.

Lymphatic capillaries are simple endothelial tubes that form a complex network in tissues. Beginning blindly, the capillaries may vary greatly in size ranging from a diameter of about a few microns to about a millimeter. Ordinarily, these capillaries do not contain valves. The network of capillaries is most dense in surface layers of the body, such as in the dermis of the skin and the mucosal layers of the digestive and respiratory system. Muscles and bones, for example, exhibit a lower density of lymphatic capillaries while no lymphatic capillaries are found in the central nervous system, meninges, epidermis, and eyeball. A special category of lymphatic capillaries extends as blind ends into the intestinal villi and are known as lacteals. Lacteals are connected to the thymus. During fat absorption from the intestine, the lymph within lacteals becomes milky in appearance and is called chyle.

The lymphatic capillaries convey lymph to larger lymph vessels (lymphatics) which resemble veins in structure but have thinner walls and more valves. The lymphatics also contain a large number of lymph nodes, usually about 600, at various intervals throughout the body. They are disposed in loose connective tissue between organs, the subcutaneous and subserous tissues, and in the submucosa of the digestive, respiratory, and urogenital tracts. Shallow lymphatics of the skin generally follow veins, while deeper lymphatics generally follow arteries. The lymphatics serve to deliver lymph throughout the body and return proteins to the cardiovascular system when they leak out of blood capillaries. Lymphatics also transport fats from the gastrointestinal tract to the blood. Lymph flow is effected by the milking action of the muscle tissues of the body on the adjacent or contained lymphatic capillaries and vessels. Valves insure that lymph is conveyed in the correct direction.

Lymphatic nodes are typically bean-shaped collections of lymphatic tissue interposed in the course of lymphatic vessels. The tissue of the node is enclosed in a strong fibroelastic capsule. Trabeculae originate from the capsule and into the node to divide the node into several compartments. A network of reticular fibers with reticulo-endothelial cells extends from the trabeculae to all parts of the node. The cortex, i.e., the outer part of the node, contains closely packed masses of lymphocytes and lymph follicles. Several afferent lymphatic vessels enter the node on its convex surface and release lymph into the sinuses of the node. As the lymph slowly moves through the node, reticuloendothelial cells filter out foreign particles such as bacteria via phagocytosis. As a result, foreign particles are prevented from entering the bloodstream. In addition, lymphocytes produced in the germinal centers of the lymph follicles are introduced into the lymph stream. Efferent lymphatic vessels at the node's hilum located on the nodes' concave surface allow lymph to leave the node to continue toward the venous system. Valves disposed in the afferent and efferent lymphatic vessels insure proper lymph flow direction. Blood vessels interface with the node at the hilum.

In sum, lymph nodes provide a key component for the proper immunological function of mammals. In humans, lymph nodes can be found in a high concentration in the face and neck, the arm pits, the thoracic cavity, the intestines and groin, the elbows, and the knees. Many different types of lymphocytes are produced by these nodes in the human body. Some lymphocytes (T cells) destroy infectious agents directly or indirectly by releasing various substances. Other lymphocytes (B cells) differentiate into plasma cells that secrete antibodies against foreign substances to help eliminate them. The spleen, thymus and tonsils are the lymphatic organs which produce B-cells, T-cells, and lymphocytes, respectively, and, with antibodies, complete the lymphatic system immunologic defenses. Importantly for cancer patients, lymphatic tissue functions in surveillance and defense against foreign cells, microbes, and cancer cells and other pathogens, as is discussed infra.

A compromised lymphatic system is associated with disease and pain as many lymph nodes and other components of the lymphatic system are located at or near nerve endings. Lymphedema, for example, is a disorder of the lymphatic system wherein excess lymph is accumulated. Such undesirable accumulation causes swelling in different part throughout the entire body including, but not limited to, the arm(s) and/or leg(s). Generally, lymphedema can develop when lymph vessels are missing or impaired, when lymph vessels are damaged, or when lymph nodes are removed. In essence, lymphedema results when the amount of lymph exceeds local lymphatic transport capacity and an abnormal amount of protein-rich fluid collects in the tissues of the effected area. It is important to emphasize that if left untreated, this stagnant protein-rich fluid causes tissue channels to increase in size and number, reduces oxygen availability in the transport system, interferes with wound healing, and provides a medium in which bacteria can incubate and proliferate, resulting in lymphangitis. The reduction of oxygen will cause lymph nodes to restrict the flow resulting from lymphatic drainage. Moreover, such swelling may cause or aggravate hernias.

In addition, cancer is often associated with lymphedema. Many cancer patients undergo surgery or radiation therapy to eliminate the cancerous growth. Surgery may remove lymph nodes, particularly if cancerous cells are identified in the lymph nodes, and lymphedema may occur as a result. In addition, radiation therapy will lead to an edema of irradiated soft tissues and lymphedema of any irradiated lymphatic tissue. Lymphedema is generally the more serious of these two side effects, because of the importance of the patient's lymphatic system to continued immune function and general health. However, repetition of radiation therapy can both further and prolong lymphedema, frequently making it a progressively more severe side effect. In addition, chemotherapy following surgery may also worsen lymphedema if administered to an already affected area.

Symptomatically, edema and lymphedema may be particularly pronounced in the upper torso due to radiation treatment of cancers of the head and neck, lungs, breast and the lymphatic system. Strong and frequent upper body radiation may cause fibrosis of the jaw and neck with excessive fibroblast deposition, thus virtually immobilizing patients and requiring such patients to be fed with a straw. Fibrosis of the upper arm may also occur with continuing radiation treatment thereby limiting the range of motion for the affected limb(s). In addition, new tumors may emerge in the edematous limbs and other portions of the lymphatic system because tumor cells, given the reduced lymph flows, lymphocyte production and ion exchange in these radiation-induced immunologically compromised edematous body parts, may take root and grow.

Lymphedema is treated through a variety of regimens with varying degrees of success. Such regimens often involve compression therapy or mechanical action. For example, U.S. Pat. No. 5,672,148 to Maunier describes a hydraulic device for lymphatic drainage and massage of the human body. This reference is directed to a device that can transmit a large variety of pressure ranges over any portion of the body with pressure profiles adapted to effect desired lymphatic drainage. It may be possible to improve lymphatic circulation, as described in U.S. Pat. No. 5,940,888 to Sher, by wearing a lymphatic circulation enhancer attached under the side panels of a woman's brassier. The enhancer comprises a lattice framework having a plurality of raised protuberances projecting outward therefrom. Such lymphatic circulation enhancers are described to provide relief from constriction of the lymph system by a woman's bra. Such devices suffer from the limitation that non-surface portions of the lymphatic system, e.g., the portion within the rib cage, are unaffected through device use.

Pharmacologically active agents may also effect lymph node drainage or activity. For example, U.S. Pat. No. 5,753, 237 to Daynes et al. describes a method of augmenting immunological responses by administering a vaccine comprising an immunizing agent and a vaccine adjuvant of dihydroepiandrosterone sulfate (DHEAS) or 16α-bromo-DHEAS. It is described that such administration of the adjuvant and the immunizing agent may drain a lymph node. In addition, U.S. Pat. No. 5,595,743 to Wu describes a process for preparing an herbal medicine. The process involves forming a mass from raw material, finely grinding the mass to make average size of suspended particles less than 50 μm, hydrolyzing the ground material by using a particular multi-enzyme system, and sterilizing the hydrolyzed material. By using poria, pinellia tube, pilose asiabell root, immature bitter orange, green tangerine orange peel, atrac tylodes rhizome, fresh ginger, oldenlandia and lonicera japonica flow in a proper proportion as raw material, the herbal medicine produced by this method is described by Wu as capable of inhibiting edema and improving cell activity of T lymphocyte cell.

Lymphedema may also be treated by application of an interferential microcurrent electrical waves. For example, U.S. Pat. No. 5,817,138 to Suzuki describes a method for treating a patient having lymphedema to improve lymphatic flow. The method involves providing multiple pairs of electrodes, each pair of electrodes connected to an electrical source defining a channel to provide a micro current of electricity across patient tissue, and positioning four or more pairs of electrodes on the patient, each electrode proximal to a center of lymph nodes. Then, a controlled current from about 20 μA to about 200 μA is provided to each channel at a frequency of up to 300 Hz. In addition, a first frequency is provided to at a first channel and a second frequency is provided to another channel to create an interferential wave form. Finally, pulsed electrical currents are passed through the patient's body using a wave form envelope with a mandatory pause between pulses. This reference also describes incorporation of the electrodes in gloves such that massaging movement may be applied during application of the micro currents.

Beside lymphedema, the lymphatic system is associated with autoimmune diseases such as rheumatoid arthritis (RA). In RA, as with other autoimmune diseases, a patient becomes immunologically sensitive to an antigenic material in his or her own body. The primary symptom of RA is inflammation of the synovial membrane, wherein the membrane thickens and synovial fluid accumulates. The resulting pressure causes pain and tenderness. As lymphocytes and macrophages learn to react to these unknown "self-antigens," they accumulate in the target organ, i.e., the synovial tissue, a hydrated sack which functions as a cushion and a lubricated bearing between the joints of the skeleton. The macrophages release small amounts of nitrous acid. Together with released free radicals and nitrosylated tyrosine residues of various proteins and polypeptides, these materials are strongly cytotoxic and produce a pannus of necrosis within the synovium, which adheres to the articular cartilage. Pannus formation sometimes erodes the cartilage completely. When the cartilage is destroyed, fibrous tissue joins the exposed bone ends. The tissue then ossifies and fuses the joint so that it is immovable, leading to a failure of the targeted joint, thereby crippling the patient in use of the afflicted limb. It is described that such arthritis may be treated by injecting a preparation comprising a pressure treated autoimmune specific T cell composition. See U.S. Pat. No. 4,996,1984 to Cohen et al. Such a composition may be prepared using T lymphocyte mitogen activated lymph node cells.

The lymphatic system has also been linked with obesity control. U.S. Pat. No. 5,391,143 to Kensey describes an implantable system for effective removal of fat or other components carried by the lymphatic system from a body by draining some lymphatic fluid from the body. The reference describes that the system may remove fat continually over a protracted period of time from the lymphatic fluid.

It is evident that current methods for effecting healing that involve the lymphatic system require mechanical action, interferential electrical microcurrents, pharmacologically active agents, and/or invasive procedures. Thus, there is a need to provide a new noninvasive method to treat conditions resulting from lymphatic disorders.

SUMMARY OF THE INVENTION

Accordingly, it is an object of the present invention to overcome the above-mentioned disadvantages of the prior art by providing a new method that noninvasively detects and activates the lymphatic system in treating disease and alleviating pain without side or after effects that characterize many other lymphatic treatments.

It is another object of the invention to provide a method to drain a portion of a lymphatic system of a living mammalian body to promote proper functioning of immunological response to pathogens.

Additional objects, advantages and novel features of the invention will be set forth in part in the description which follows, and in part will become apparent to those skilled in the art upon examination of the following, or may be learned by practice of the invention.

In one aspect, then, the present invention generally relates a non-invasive method for alleviating a disorder associated with a lymph node in a living mammalian body. The method calls for physical contact with a stimulation source to be provided simultaneously at the closest exterior body surface to the lymph node and at an opposing body surface. Once in place, the stimulation source transfers energy to the closest exterior body surface so as to induce localized pulsations that characterize the activation of the lymph node. In certain instances, the energy transfer stimulates a diseased lymph node. For optimal results, energy is continuously transferred until the localized pulsations substantially subside. This non-invasive method is particularly suited for use without anesthesia and applicable to a non-surface lymph node, i.e., one that is located is closer to an artery than a vein.

In another aspect, the invention relates to the method as above, wherein the stimulation source has a substantially constant temperature in a range from about 30° C. to about 45° C. and contacting the closest exterior body surface with the source. In addition, the simulation may cause the simulated area to increase in temperature.

In still another aspect, the invention relates to the method as above, wherein the closest exterior body surface contacts a source surface adapted to conform to the closest exterior body surface. In addition, the opposing body surface may also contact another source surface adapted to conform to the opposing body surface. The source surface may comprise a flexible and/or organic flexible material.

In a further aspect, the invention relates to the method as above, wherein contact is provided at a time to an area of about 1 $cm^2$ to about 400 $cm^2$ of the closest exterior body surface.

In a still further aspect, the invention relates to the method as above wherein non-thermal energy is transferred to the closest exterior body surface. The non-thermal energy may be electrical or magnetic.

In another aspect, the invention relates to the method as above, wherein the living mammalian body having the disorder is human. The living mammalian body may exhibit edema such as lymphedema, cancer, auto-immune diseases such rheumatoid arthritis or obesity. In addition, the living mammalian body may have undergone other treatment for cancer such as radiation therapy, chemotherapy or surgery.

In still another aspect, the invention relates to the method as above, wherein the stimulation source is the hand or other body part of a human individual. Preferably, the individual establishes physical contact between the closest exterior body surface and his or her hand or fingertip. In addition, contact may be established between the opposing body surface and the other hand of the individual. Preferably, the individual can detect the localized pulsations through tactile sensations and/or as sounds.

In a further aspect, the invention generally relates to a noninvasive method for draining a portion of a lymphatic system in a living mammalian body. The method involves providing physical contact with a stimulation source simultaneously at an exterior body surface that exhibits a symptom due to blockage of the portion of the lymphatic system and at an opposing body surface with respect to the exterior body surface. Once contact is established, energy is transferred from the stimulation source to the exterior body surface to induce localized pulsations that characterize lymphatic activation and drainage. The energy may be magnetic, electrical, possibly thermal or some other type of energy. Energy is transferred to the closest exterior body surface until lymphatic healing is complete.

In a still further aspect, the invention generally relates to a noninvasive method for alleviating discomfort such a pain associated with a malfunctioning portion of a lymphatic system in a living mammalian body. The method involves providing physical contact with a stimulation source simultaneously at the closest exterior body surface to a healthy portion of the lymphatic system and at an opposing body surface with respect to the exterior body surface. Once such contact is established, energy is transferred from the stimulation source to the closest exterior body surface to induce localized pulsations that characterize the activation and drainage of the malfunctioning portion of the lymphatic system.

DETAILED DESCRIPTION OF THE INVENTION

Figure 1A:
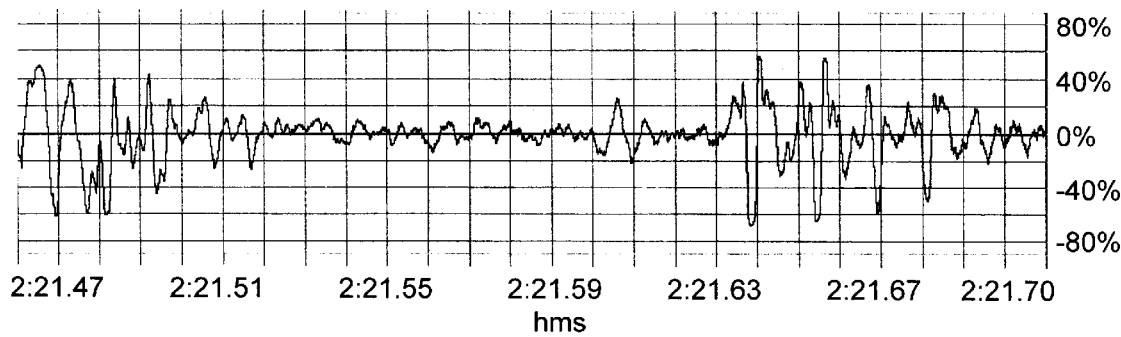
FIGS. 1A–1C, collectively referred to as FIG. 1, are graphical representations of digitized sound recordings of pulsations associated with a diseased lacteal lymph node recorded before, during and after treatment, respectively.

Before describing the invention in detail, it must be noted that, as used in this specification and the appended claims, the singular forms "a," "an," and "the" include plural referents unless the context clearly dictates otherwise. Thus, for example, reference to "a lymph node" includes more than one lymph node, reference to "a stimulation source surface" includes a plurality of stimulation source surfaces and the like.

In describing and claiming the present invention, the following terminology will be used in accordance with the definitions set out below.

The term "activate" as used herein refers to the inducing of a portion of the lymphatic system to engage in activity that characterizes healthy functioning of that portion. For example, activating a lymph node involves inducing the lymph node to produce lymphocytes and effect filtration of lymph, and activating a portion of the lymphatic system having valves involves opening valves along the lymphatics to effect proper lymph flow. Activation is typically accompanied by localized pulsations.

The term "localized pulsations" is used herein to refer to a substantially rhythmic throbbing or vibration in a mammalian body, wherein the substantially rhythmic throbbing is detectable near the source of the pulsation. Depending on the intensity at the source of the pulsation, localized pulsations are typically detectable only at a portion of the body surface near the source of the pulsation, i.e., a malfunctioning portion of the lymphatic system, typically a lymph node. Without invasive means, the localized pulsations are typically most easily detected at the closest exterior body surface to the source of the pulsation and sometimes, to a lesser degree, at the opposing body surface with respect to the closest exterior body surface.

The term "obese" as used herein refers to a state of a mammalian body in which the ratio of fat to lean body mass is at least about 20 percent higher than the accepted norm for healthy functioning of the body.

The term "opposing body surface with respect to the closest exterior body surface" as used herein refers to the location on the body surface that intersects a line extending through both the interior of the body affected by a lymphatic disorder and the closest exterior body surface thereto.

The term "physical contact" as used herein refers to the contact between two bodies such that the surfaces of the bodies are substantially immobile with respect to each other. In other words, the surfaces of the bodies may exhibit only slight movement with respect to each other. In addition, pressure between the contacting surfaces is maintained at a substantially constant level. Ordinary massage techniques, acupressure, and other forms of motion is neither desirable nor required for physical contact.

The term "stimulation source" as used herein refers to a body that is capable of conducting energy to another body surface. Energy from the stimulation source may be electrical, magnetic, thermal or of a yet unidentified character that, when applied to an affected portion of the lymphatic system, promotes lymphatic activation and healing that is characterized by localized pulsations.

It is known that many mammalian ailments are associated with the lymphatic system and, in particular, with a lymph node within the body. Examples of these disorders include, but are not limited to, arthritis, cancer, obesity, and lymphedema. These disorders are conventionally treated by various regimens. For example, treatments for cancer include various forms of surgery, chemotherapy, and radiation therapy. Obesity can be treated, e.g., through restricting calorie intake, increasing physical activity and liposuction. Many of these ailments are associated with a disorder of the lymphatic system, wherein the disorder is associated with a lymph node in the mammalian body or with a portion of the lymphatic system in need of drainage. Notably, it has now been discovered that many of these disorders are associated with a lymph node or a portion of the lymphatic system that may be activated or drained through energy transfer that promotes healing as evidenced by pulsations in response to the transferred energy. These pulsations form a basis of the invention which allows noninvasive detection and activation of the lymphatic system in treating disease and alleviating pain.

One aspect of the invention involves a non-invasive method for alleviating a disorder associated with a lymph node in a living mammalian body. In order to provide relief to a lymph node disorder, it is often important to detect the malfunctioning or inactive lymph node associated with the disorder. Detection can be accomplished in a number of ways depending on the symptoms of the disorder. For example, lymphedema, as describe above, results when the amount of lymph in a portion of the lymphatic system exceeds its lymphatic transport capacity and an abnormal amount of protein-rich fluid collects in the tissues of the effected area. As a result, swelling occurs in the effected area. The swelling may provide a generalized indication of the location of one or more diseased, damaged or inactive lymph nodes. Swelling may develop in three stages, ranging from mild to severe. Stage 1 lymphedema exhibits the mildest form of swelling that is spontaneously reversible. The affected tissue is still at the "pitting" stage, which means that when pressure is applied by fingertips, the area indents and holds the indentation. Stage 2 lymphedema exhibits spontaneously irreversible swelling in which affected tissue has a spongy consistency and is non-pitting. When pressed by fingertips, the tissue bounces back without any indentation forming. Stage 2 lymphedema may mark the beginning of the hardening of affected tissue through fibrosis leading to stage 3 lymphedema, commonly referred to as lymphostatic elephantiasis. Stage 3 is the most severe form of lymphedema and is characterized by extreme irreversible swelling, particularly when limbs are affected. Affected tissue is hard, fibrotic, and unresponsive fingertip pressure. The severity of swelling in stages may also provide insight into the severity of lymph node disorder.

In addition to detecting swelling through visual or tactile inspection as described above, lymphedema and associated diseased lymph nodes can be detected by evaluation of other symptoms. When lymphedema remains untreated, accumulated protein—rich fluid provides an ideal culture medium for bacteria or other sources of infection leading to lymphangitis. Symptoms of lymphangitis may include some or all of the following: rash; red blotchy skin; itching of the effected area; discoloration; increase of swelling and/or temperature of the skin; an unusually heavy sensation of the affected area; pain; and sudden onset of high fevers or chills. Because infection tends to indicate prolonged and untreated lymphedema, such areas of infection may allow detection of severely diseased lymph nodes.

When external indications of diseased lymph nodes are not readily apparent or when more specific information relating to a lymph node is needed, more sophisticated methods of detection may be used. One such method of detection is described in U.S. Pat. No. 4,827,945 to Groman et al. This patent describes the use of superparamagnetic metal oxide materials exhibiting certain magnetic and biological properties which make them uniquely suitable for use as magnetic resonance imaging (MRI) agents to enhance MRI images of human organs and tissues. These agents may be coated with biological molecules to target specific organs or tissues such that, upon administration to an animal, the agents are collected in the target organs. The MRI agents are administered by various routes but are typically injected directly into the animal's bloodstream.

In addition, radiation-based methods for locating lymph nodes are known. For example, U.S. Pat. No. 5,732,704 to Thurston et al. describes a method for identifying a sentinel node located within a grouping of regional nodes at a lymph drainage basin associated with neoplastic tissue such as those found in cancerous tumors. The sentinel node is the nearest lymph node to the site of the neoplastic tissue and within the pertinent lymph drainage basin. Such a node, being on the most direct drainage pathway, will present the most likely site of early metastasis. The method, like other radiation-based detection methods, requires a radiopharmaceutical to be injected at the situs of the neoplastic tissue. This radiopharmaceutical migrates along a lymph duct toward the drainage basin containing the sentinel node. The sentinel node is located where detected radiation intensity is at a local maximum. U.S. Pat. No. 5,961,458 to Carroll describes a minimally invasive surgical probe for detecting and removing radioactively tagged tissue, e.g., a sentinel lymph node within the body of a living being.

The present invention in one aspect requires that a stimulation source be placed in physical contact with the closest exterior body surface lymphatic tissue affected by the disorder. In order to determine the closest exterior body surface, any of the above methods can be used, e.g., monitoring external swelling, detecting temperature change, assessing level of pain, or tagging affected lymphatic tissue with radiopharmaceuticals or magnetic media. However, none of these methods is an ideal substitute for detecting pulsations that occur only when a malfunctioning portion of the lymphatic responses to energy transfer from a stimulation source as described below. In other words, external swelling is not necessarily an indication of a lymphatic disorder characterized by localized pulsations. To detect such pulsations by touch, one of typically places a hand on the external surface of the affected body. The hand, usually the palm side, is slid across the surface to sense the area on which the pulsations are most strongly detected. Fingertips are particularly sensitive to such pulsations. Touch may involve direct skin to skin contact or contact through clothing or other materials.

Sometimes, when the disorder is severe, the pulsation can also be detected as sound, in which case physical contact is helpful to locate the precise location where the pulsations are strongest. Alternatively, a sound detector may be employed. Such sounds may be recorded by employing a microphone at or near the area of treatment, before, during or after treatment. Graphical representations of digitized sound recordings of pulsations associated with a diseased lymph node recorded before, during and after the application of the simulation source to the affected area are shown in FIGS. 1 and 2. The ordinate axes of the figures represent time and the abscissa axes of the figures represent the amplitude of recorded sound. The sound recordings were made through the use of a contact microphone substantially immobilized with respect to exterior surfaces of a female human subject near a dysfunctional lymph node. Such contact microphones are well known in the art and are commercially available from a number of manufacturers and vendors. These figures are representative of sounds recorded from individuals receiving treatment according to the method of the invention, on an on-going basis. Pulsation intensity is strongly correlated with the amplitude of the recorded sound.

Figure 1B:
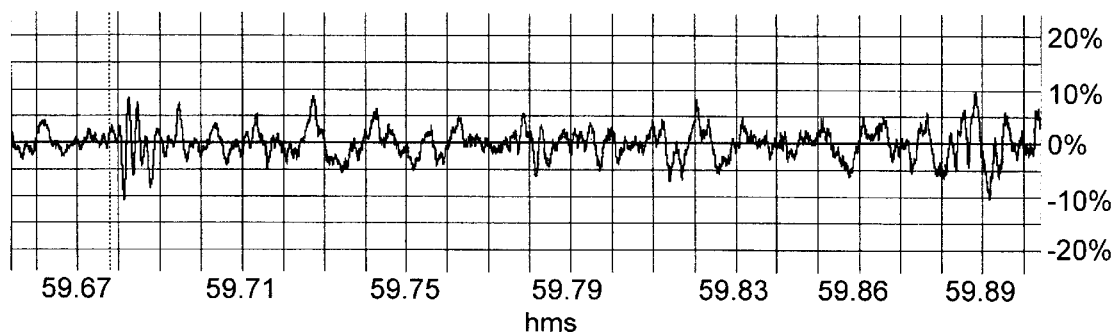
Figure 1C:
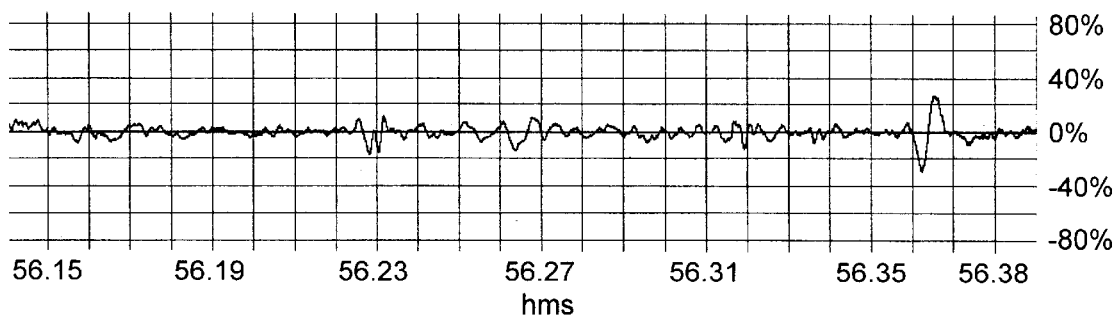

It is evident from FIGS. 1 and 2 that there are significant differences between the pulsations recorded before, during and after treatment. As shown in FIGS. 1A and 1B, pulsations recorded before treatment exhibit an overall greater amplitude than pulsations recorded during treatment. In addition, as shown in FIGS. 1B and 1C, pulsations recorded during treatment exhibit an overall greater amplitude than pulsations recorded after treatment. In other words, attenuation of the pulsations associated with a lymph node disorder is achieved through the practice of the inventive method. Further, FIG. 1 indicates that treatment employing the inventive method results in pulsations having a greater regularity in frequency and amplitude than the pulsations recorded before treatment. As the pulsations are reduced during treatment, it is evident that the localized pulsations indicative of a lymphatic disorder are more irregular than pulsations present in a healthy body and associated with ordinary vital functions such as breathing and blood flow.

Figure 2A:
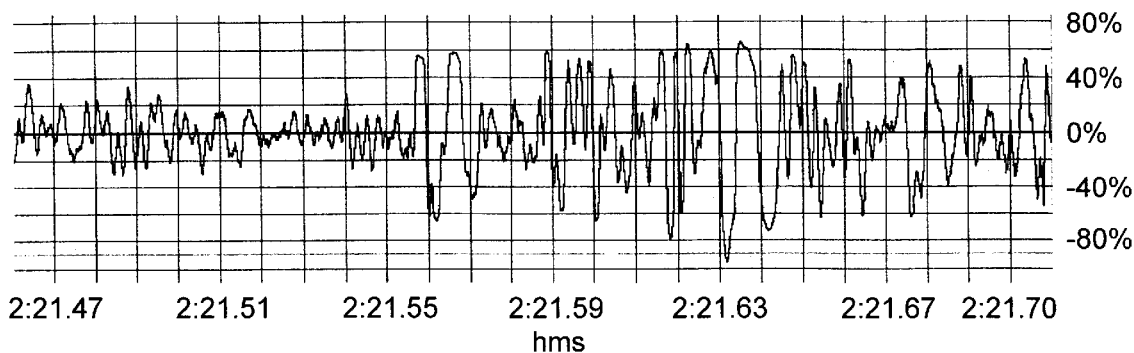
FIGS. 2A–2C, collectively referred to as FIG. 2, are graphical representations of digitized sound recordings of pulsations associated with diseased lymph nodes near the thymus recorded before, during and after treatment, respectively.
Figure 2B:
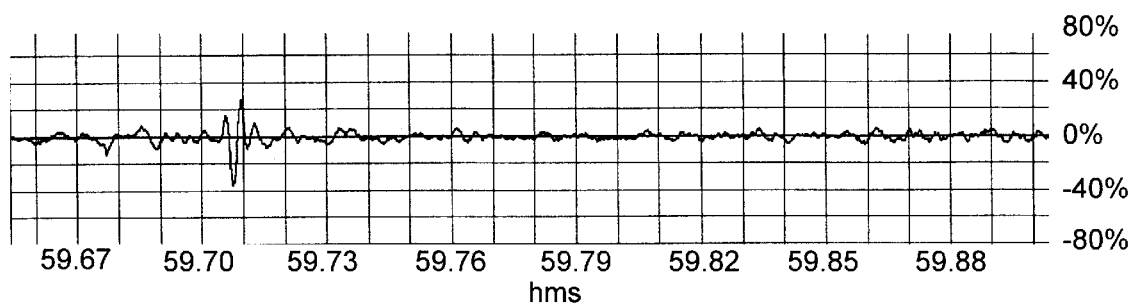
Figure 2C:
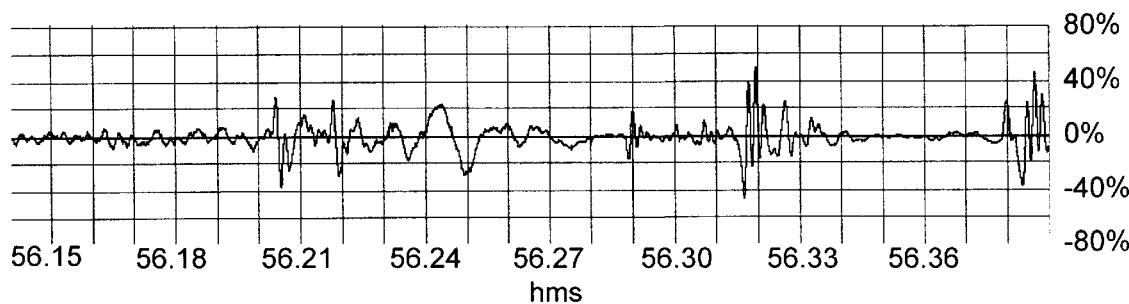

Similarly, FIG. 2 further illustrates that the present treatment method tends to result in the attenuation of pulsations. FIGS. 2A and 2B illustrate that the inventive method results in pulsation attenuation during treatment. While FIGS. 2B and 2C, when viewed together, show that there may be some recovery in amplitude of the pulsations when the treatment is stopped, it is clear that the amplitude of the pulsations after treatment, as illustrated in FIG. 2C, is lower than the amplitude of the pulsations before treatment, as illustrated in FIG. 2A. That is, overall reduction of pulsation amplitude is not limited to the duration of treatment. Typically, patients undergoing continuing treatment tend to respond more readily to the inventive treatment than those who receive treatment occasionally.

In addition, the pulsations may be detected as a palpitation. When the pulsations are present, such pulsations are recognizable by trained human touch. One who is able to detect such pulsations may train another by example, e.g., identifying individuals who suffer from the lymphatic disorder, detecting the localized pulsations, allowing the trainee to touch the affected area on the individual to feel the localized pulsations, and comparing the tactile sensation to an unaffected area or the corresponding area on an unaffected individual. Success from such training may vary with the skill of the teacher and the natural abilities of the student. In rare cases, an individual may be able to detect such pulsations without training from another. One such individual is Ms. Harumi Naganuma of San Francisco, Calif., the inventor herein, but there may be others yet to be identified who can detect such pulsations without training. It is envisioned that such pulsations may be detectable by a device yet to be built.

Once the affected lymphatic region is located, through conventional methods or by detecting pulsations, treatment of the disorder may then take place. Depending on the disorder, treatment by conventional methods may vary. For example, lymphedema can be treated through complex decongestive therapy (CDT) methods. CDT methods involve manual lymph drainage (MLD), compression therapy, remedial exercises and skin care. MLD is a manual treatment technique which improves the activity of lymph vessels by mild mechanical stretches on the wall of lymphatics and nodes where excess lymph is collected. MLD redirects the lymph flow around the blocked areas into other lymphatics that eventually drain into the venous system. Compression therapy increases pressure to affected issue and is applied between MLD treatments to prevent localized reaccumulation of lymph. Compression therapy may be performed in two phases. In the first phase, short stretch bandages are applied, and the second phase, custom-made garments are worn. When the compression bandages and garments are worn, decongestive exercises may be performed as well as respiratory therapy. These exercises assist in bringing about lymphokinetic effects of joint and muscle pumps. Finally, since infections are very common and serious complications of lymphedema, meticulous care must be taken to ensure proper skin and nail hygiene. CDT cannot be undertaken unless there is no sign of lymphangitis. It is evident, then, that CDT is directed to lymphatic drainage at the body surfaces, since activity such as MLD and compression therapy cannot affect lymph nodes located deep within the interior of a body, e.g., closer to an artery than a vein or located within the rib cage.

In addition, treatment for lymphatic disorders may involve removal of lymph fluids from the mammalian body by using catheters such as those described in U.S. Pat. No. 4,957,484 to Murfeldt. This reference describes a device for accessing a thoracic duct or right lymphatic duct to withdraw lymph therefrom. In addition, obesity control may also be effected by removing a fat-like material from the lymphatic fluid continually over a protracted period of time through an implantable system. See Kensey et al. It is apparent that such drainage techniques involve invasive procedures that require tissue perforation.

In contrast, the invention does not involve invasive procedures but nevertheless brings about drainage and healing of lymph nodes that are positioned deep within the body. A stimulation source, is placed in physical contact with closest surface to the affected portion. Simultaneously, the stimulation source is contacted with the opposing body surface with respect to the closest exterior body surface. As a result, energy from the stimulation source is transferred to the closest exterior body surface. Energy may also be transferred to the opposing body surface as well. Transferred energy is believed to be magnetic, but may in certain instances involve another form of energy by itself or in combination with thermal energy, infrared energy, magnetic energy electrical energy or another yet to be identified form of energy that promotes lymphatic healing. Beside inducing pulsations in the affected area, energy transfer result in generation of heat by the affected area. Typically, the temperature of the closest exterior body surface to the lymph node is raised. Preferably the temperature of the closest exterior body surface is raised by at least 1° C. Optimally, the temperature of the closes exterior body surface is raised by about 1° C. to about 2° C. Moreover, it is believed that for enhanced performance, the stimulation source may have a substantially constant temperature in a range of about 30° C. to about 45° C., more preferably about 30° C. to about 40° C. Optimally, the substantially constant temperature is about 35° C. to about 37° C. The transfer of energy is typically a mild process that requires continuous contact for a significant amount of time depending on the severity of the disorder.

For mild lymphatic disorders, required contact time may range from about a few minutes to about an hour. Effective treatment for severe lymphatic disorders may require physical contact over at least an hour, and in certain instances, several hours. During contact and energy transfer, a portion of the lymphatic system, typically the lymph node, is activated and drained. Multiple sessions of treatment through an extended period of time may be necessary in extremely severe cases. For example, a patient may require a series of weekly, biweekly or monthly treatment session each lasting from about one to several hours for a case severe lymphatic disorder. The entire series of treatment may take place within a time span of weeks to years, depending on the severity of the disorder.

As the method of the invention brings about drainage and healing of lymph nodes, it is believed that the inventive method may contribute to the elimination of damaged and/or diseased cells. Such damaged and/or diseased cells or portions thereof are conveyed into the lymphatic system and ultimately eliminated as waste from a mammalian body. While not wishing to be bound by theory, it is believed that the inventive method allows the transferred energy to stimulate the mitochondria of nearby healthy cells to efficiently and effectively engage in producing and regulating energy, thereby maintaining the overall well-being of such cells. During this process, DNA in the nuclei of healthy cells "divides" and replicates, forming additional healthy cells. Such division is often accompanied with cell growth to displace the damaged and/or diseased cells that are eliminated through the lymphatic system.

In addition, the stimulation source may have a surface adapted to conform to the contours of bodies affected with a lymphatic disorder. Generally, physical contact is established with the closest surface to the affected region, wherein the contact area occupies about 1 cm² to about 400 cm². More typically, the contact area covers about 1 cm² to about 250 cm². Such a surface may be flexible or elastic, like a human finger. Importantly, the pressure associated with contact ideally should not cause substantial blanching of the tissue near the area of contact. By "blanching" it is meant that body fluid such as blood or lymph is occluded from a region of tissue such that the region is drained of color and appears white. Thus, surfaces with a hard and sharp protrusion may not be suitable for contact with the body. The protrusion may cause localized tissue blanching. When the energy transfer is effected by one more human fingers, it is generally preferable that contact with the effected body is established with the palm side of the fingers when area of body being contacted is convex. The palm side of the human hand is generally more easily adaptable for conformal contact with a convex surface. The back side of the human hand, however, may be more adaptable for conformal contact with some concave surfaces. Both surfaces of the hand may be used simultaneously in some instances. Fingertips are optimal for contact in most instances.

From the above discussion, it is evident that the invention relates to a non-invasive method for alleviating a disorder associated with a portion of the lymphatic system such as a lymph node in a living mammalian body, wherein contact is established with the living mammalian body such that energy is transferred to the body. The method may be used to treat conditions from which mammals, e.g., humans, dogs, cats, horses, cattle, etc., may suffer. Such conditions include, but are not limited to, edemas such as lymphedema, deleterious effects resulting from treatment from cancer such as radiation therapy, chemotherapy, or surgery, auto-immune diseases such as rheumatoid and other types of arthritis, and obesity. More specifically, diseases that have been treated using the present inventive process that have resulted in partial or near complete healing include, but are not limited to, cataract, glaucoma, fundus hemorrhage, retinal detachment, amblyopia, facial palsy, otitis, tonsillitis, vertigo, sonitus, rhinitis, allergic rhinitis, taste disorder, laryngeal cancer, alopecia, eczema, urticaria, herpes zoster, herpes simplex, atopic dermatitis, vascular dementia, senile dementia of Alzheimer type, schizophrenia, depression, neurosis, autonomic imbalance, neurosis, insomnia, tonsillitis, glomerular nephritis, constipation, irregular electroencephalogram, atopy, high fever, common cold, influenza, headache, Parkinson's disease, pollinosis, bronchitis, bronchial asthma, pneumonia, pulmonary emphysema, lung cancer, gastritis, gastritis ulcer, duodenal ulcer, gastric cancer, large intestine polyp, hepatitis (acute or otherwise), liver cancer, liver cirrhosis, gall stone, pancreatitis, pancreas cancer, esophagus cancer, leukemia, anemia, lymphoma (malignant or otherwise), immunologic deficiency syndrome, thrombocytopenia, angina pectoris, myocardial infarction, heart failure, hypertension, arteriosclerosis, varix, varicosity, sciatic neuritis, intercostal neuralgia, nephritis, renal failure, osteoporosis, diabetes mellirus, thyroid adenoma, nephritis, lung cancer, high blood pressure, arrhythmia, gastric ulcer, duodenal ulcer, gastric cancer, intestinal polyp, large intestine cancer, cholecystitis, gallbladder cancer, pancreatic cancer, diarrhea, constipation, hernia, cerebral hemorrhage, cerebral infarction, brain tumor, brain ischemia, hydrocephaly, fracture, dislocation, sprain, tennis elbow, baseball elbow, cervical spondylosis, frozen shoulder, osteoporosis, herniation of the intervertebral disc, lumbago, lower back pain, sciatic neuritis, intercostal neuralgia, stiff shoulders, muscular pain, muscle fragmentation, shrunken Achilles tendon, sprained finger, gout, whiplash cervical injury, transformation of bone, uterine myoma, uterus cancer, amenorrhea, mastitis, breast cancer, periodontitis, pulpitis, dental caries, stomatitis, test disorder, abnormal bite occlusion, urethral stone, cystitis, prostate cancer, urethritis, and nocturnal enuresis.

In addition, it is apparent that contact with such a living mammalian body may be provided with a human individual, specifically, with one or both hands of the individual. Depending on the condition, energy transfer may be ceased when an event occurs. For example, when energy is transferred in order to alleviate a disorder associated with a lymph node, wherein the disorder is characterized by localized pulsations at the closest exterior body surface, energy transfer may be terminated when the localized pulsations are no longer detectable. Similarly, when energy transfer is effected to drain a portion of a lymphatic system, energy transfer may be terminated when at least some lymphatic drainage has occurred at the desired portion of the lymphatic system. Moreover, if energy is transferred to alleviate pain, pain elimination may signal that energy transfer should be terminated. As a general matter, then, there are a variety of indications of successful of lymphatic treatment using the inventive method. These indications include, but are not limited to: (1) softening of hardened affected lymphatic regions; (2) a gurgling sound associated with of lymphatic decongestion; (3) a noise that accompany improved vein and/or arterial flow; (4) a clicking bone connecting sound; (5) prickly sensation experienced by a patient that accompanies healing of nerves; (6) recovery of muscle mass; (7) pain elimination; (8) subsiding of swelling; (9) improved breathing; (10) improved oxygen transport to the lungs, stomach and other organs; (11) relaxation of organ stress (12) hydrocephaly reduction; and (13) reduced fever.

Accordingly, the present invention provides a new method for alleviating a disorder associated with a portion of the lymphatic system such as a lymph node in a living mammalian body condition. A number of important and heretofore unrealized advantages have now been achieved that include, but are not limited to, the following:

the method is non-invasive in nature, and undesirable effects resulting from surgical procedures, e.g., infection, pain and adverse reaction to anaesthesia, are eliminated;

the method requires no pharmacologically active agent and thus eliminates the possibility of adverse reactions to such agents, e.g., allergic or autoimmune responses or adverse drug interactions.

the method does not require complicated electrical or mechanical apparati that may fail due to faulty electrical connections or wear and tear; and unlike CDT, the method may be carried out even when the patient suffers from lymphangitis or blockage of non-surface lymph nodes.

It is to be understood that while the invention has been described in conjunction with the preferred specific embodiments thereof, that the foregoing description is intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

I claim:

1. A noninvasive method for alleviating a disorder associated with a lymph node in a living mammalian body, the method comprising:
   (a) providing physical contact with a stimulation source simultaneously at the closest exterior body surface to the lymph node and an opposing body surface with respect to the exterior body surface;
   (b) transferring energy from the stimulation source to the closest exterior body surface so as to induce localized pulsations that characterize the activation of the lymph node; and
   (c) sensing localized pulsations then ceasing energy transfer when the localized pulsations cease.

2. The method of claim 1, wherein the living mammalian body is not anaesthetized.

3. The method of claim 1, wherein the lymph node is located closer to an artery than a vein.

4. The method of claim 3 wherein the lymph node is located within the rib cage.

5. The method of claim 1, wherein the stimulation source has a substantially constant temperature in the range of about 34° C. to about 40° C.

6. The method of claim 1, further comprising raising the temperature of the closest exterior body surface.

7. The method of claim 6, wherein the temperature of the closest exterior body surface is raised by about 1° C. to about 2° C.

8. The method of claim 1, wherein the physical contact of step (b) is provided to an area of about 1 cm$^2$ to about 400 cm$^2$ of the closest exterior body surface.

9. The method of claim 8, wherein the area is about 1 cm$^2$ to about 250 cm$^2$.

10. The method of claim 1, wherein the stimulation source comprises a contact surface that is composed of an organic flexible material.

11. The method of 5, wherein the stimulation source is capable of sensing the localized pulsations.

12. The method of claim 1, step (b) comprises transferring a non-thermal energy to the closest exterior body surface.

13. The method of claim 12, wherein the non-thermal energy is magnetic.

14. The method of claim 13, wherein the non-thermal energy is electrical.

15. The method of claim 1, wherein the living mammalian body is human.

16. The method of claim 1, wherein the living mammalian body exhibits edema.

17. The method of claim 16, wherein the edema is lymphedema.

18. The method of claim 1, wherein the living mammalian body exhibits cancer.

19. The method of claim 1, wherein the living mammalian body has undergone treatment for cancer.

20. The method of claim 19, wherein the treatment for cancer comprises radiation therapy, chemotherapy or surgery.

21. The method of claim 1, wherein the living mammalian body exhibits an autoimmune disease.

22. The method of claim 21, where the autoimmune disease is rheumatoid arthritis.

23. The method of claim 1, wherein the living mammalian body is obese.

24. The method of claim 4, wherein the source is an individual.

25. The method of claim 24, wherein the individual is human.

26. The method of claim 25, wherein step (a) comprises establishing static physical contact between the closest exterior body surface and a fingertip of the individual.

27. The method of claim 25, wherein step (a) comprises establishing contact between the opposing body surface and a hand of the individual.

28. The method of claim wherein step (a) comprises establishing physical contact between the closest exterior body surface and a fingertip of the individual.

29. The method of claim 25, wherein the localized pulsations are detectable through tactile sensations.

30. The method of claim 25 wherein the localized pulsations are detectable by the individual as a sound.

31. The method of claim 30 wherein the sound characterizes decongestion of a portion of the lymphatic system.

32. The method of claim 30, wherein the sound characterizes improved blood flow.

33. The method of claim 30, wherein the sound characterizes improved lymph flow.

34. A noninvasive method for draining a portion of a lymphatic system in a living mammalian body, the method comprising:
   (a) providing physical contact with a stimulation source simultaneously at an exterior body surface that exhibits a symptom due to blockage of the portion of the lymphatic system and at an opposing body surface with respect to the exterior body surface;
   (b) transferring energy from the stimulation source to the exterior body surface to induce localized pulsations that characterize lymphatic activation and drainage; and
   (c) sensing localized pulsations then ceasing energy transfer when the localized pulsations cease.

35. The method of claim 34 wherein the energy is magnetic, thermal or electrical energy.

36. A noninvasive method for alleviating discomfort associated with a malfunctioning portion of a lymphatic system in a living mammalian body, the method comprising:
   (a) providing physical contact with a stimulation source simultaneously at the closest exterior body surface to a malfunctioning portion of the lymphatic system and at an opposing body surface with respect to the exterior body surface;
   (b) transferring energy from the stimulation source to the closest exterior body surface to induce localized pulsations that characterize the activation and drainage of the malfunctioning portion of the lymphatic system; and
   (c) sensing localized pulsations then ceasing energy transfer when the localized pulsations case.

37. The method of claim 36, wherein steps (a) and (b) are repeated.

38. The method of claim 37, wherein steps (a) and (b) are regularly repeated.

39. The method of claim 36, wherein the discomfort is painful.

40. A noninvasive method for detecting a malfunctioning portion of the lymphatic system in a living mammalian body, the method comprising:
   (a) providing physical contact between a stimulation source and an exterior body surface;
   (b) transferring energy from the stimulation source to the exterior body surface; and
   (c) detecting pulsations in response to the transfer of energy.

* * * * *

UNITED STATES PATENT AND TRADEMARK OFFICE
CERTIFICATE OF CORRECTION

PATENT NO.    : 6,676,686 B2
DATED         : January 13, 2004
INVENTOR(S)   : Harumi Naganuma It is certified that error appears in the above-identified patent and that said Letters Patent is hereby corrected as shown below:

<u>Column 14,</u>
Line 65, after "claim", please insert -- 25 --.

Signed and Sealed this

Twentieth Day of April, 2004

JON W. DUDAS
*Acting Director of the United States Patent and Trademark Office*